United States Patent
Yamanari

(10) Patent No.: US 9,593,936 B2
(45) Date of Patent: Mar. 14, 2017

(54) OPTICAL TOMOGRAPHIC DEVICE CAPABLE OF ACQUIRING A PLURALITY OF TOMOGRAPHIC IMAGES

(71) Applicant: Tomey Corporation, Nagoya-shi (JP)

(72) Inventor: Masahiro Yamanari, Nagoya (JP)

(73) Assignee: Tomey Corporation, Nagoya-shi (JP)

(*) Notice: Subject to any disclaimer, the term of this patent is extended or adjusted under 35 U.S.C. 154(b) by 0 days.

(21) Appl. No.: 14/849,860

(22) Filed: Sep. 10, 2015

(65) Prior Publication Data
US 2016/0069664 A1    Mar. 10, 2016

(30) Foreign Application Priority Data
Sep. 10, 2014  (JP) .................. 2014-184507

(51) Int. Cl.
  *G01B 9/02*    (2006.01)
  *A61B 3/10*    (2006.01)
  *A61B 5/00*    (2006.01)

(52) U.S. Cl.
  CPC .......... *G01B 9/02091* (2013.01); *A61B 3/102* (2013.01); *A61B 5/0066* (2013.01);
  (Continued)

(58) Field of Classification Search
  CPC ............ G01B 9/02011; G01B 9/02091; G01B 9/0209; G01B 9/02027–9/02028; A61B 5/0066; A61B 5/0073
  See application file for complete search history.

(56) References Cited

U.S. PATENT DOCUMENTS

2007/0035743 A1* 2/2007 Vakoc .................... G01N 21/21
                                                            356/495
2007/0236700 A1* 10/2007 Yun ..................... G01N 21/4795
                                                            356/491
(Continued)

FOREIGN PATENT DOCUMENTS

| JP | 4344829 B2    | 10/2009 |
| JP | 2013113587 A  | 6/2013  |
| JP | 2013148482 A  | 8/2013  |
| JP | 2014206433 A  | 10/2014 |

OTHER PUBLICATIONS

Yiheng Lim, Young-Joo Hong, Lian Duan, Masahiro Yamanari, Yoshiaki Yasumo, "Passive component based multifunctional Jones matrix swept source optical coherence tomography for Doppler and polarization imaging", Optics Letters, vol. 37, No. 11, Jun. 1, 2012 p. 1958-1960 (3 pages).

*Primary Examiner* — Michael P Lapage
(74) *Attorney, Agent, or Firm* — Shumaker, Loop & Kendrick, LLP

(57) ABSTRACT

Provided is an optical tomographic device for simultaneously acquiring a plurality of tomographic images at a same position in a subject without narrowing a depthwise measurement range. A measurement light generator generates at least two measurement lights with different optical path lengths, superimposes the at least two measurement lights, radiates the resultant light to a subject, and splits reflected light reflected from the subject into at least two reflected lights. A reference light generator generates at least two reference lights with different optical path lengths. An interfering light generator combines the at least two reflected lights and the at least two reference lights having corresponding different optical path lengths, to generate at least two interfering lights. An interfering light detector detects (Continued)

the at least two interfering lights independently by at least two interfering light detectors.

10 Claims, 5 Drawing Sheets

(52) U.S. Cl.
CPC ..... *G01B 9/02004* (2013.01); *G01B 9/02028* (2013.01); *G01B 9/02069* (2013.01); *G01B 2290/45* (2013.01); *G01B 2290/70* (2013.01)

(56) References Cited

U.S. PATENT DOCUMENTS

| | | | | |
|---|---|---|---|---|
| 2008/0140325 | A1* | 6/2008 | Teramura | G01N 21/4795 |
| | | | | 702/57 |
| 2009/0233457 | A1* | 9/2009 | Jorgensen | H01R 43/10 |
| | | | | 439/11 |
| 2012/0224165 | A1* | 9/2012 | Swanson | G01B 9/02004 |
| | | | | 356/28.5 |
| 2012/0327423 | A1 | 12/2012 | Hanebuchi | |
| 2013/0107277 | A1* | 5/2013 | Hirose | A61B 3/102 |
| | | | | 356/512 |
| 2015/0092195 | A1* | 4/2015 | Blatter | G01B 9/02091 |
| | | | | 356/479 |
| 2015/0369586 | A1* | 12/2015 | Fukuhara | G01B 9/02058 |
| | | | | 356/479 |

\* cited by examiner

OPTICAL TOMOGRAPHIC DEVICE CAPABLE OF ACQUIRING A PLURALITY OF TOMOGRAPHIC IMAGES

CROSS-REFERENCE TO RELATED APPLICATION

This application claims priority to Japanese Patent Application No. 2014-184507 filed on Sep. 10, 2014, the contents of which are hereby incorporated by reference in their entirety into the present application.

TECHNICAL FIELD

The present application relates to a device which obtains an optical tomographic image, using optical interference.

DESCRIPTION OF RELATED ART

An optical tomographic device, owing to its noninvasive and contactless characteristics, is widely used for an ophthalmic device or the like as a method for acquiring a tomographic image of body tissues.

Birefringence which changes a polarization state occurs in a structure in which molecules or fiber tissues are arranged in a constant direction. A retina in a fundus presents a strong birefringence property in a retinal nerve fiber layer, a retinal pigment epithelial layer, a blood vessel wall, a sclera, and a lamina cribrosa. Regarding polarization sensitive OCT (PS-OCT) which is one type of functional OCT (i.e., optical coherence tomography), in order to visualize these structures by a tomographic image of the birefringence property, in recent years, various types of polarization sensitive OCT have been developed. For example, optical tomographic devices of this type are disclosed in Japanese Patent No. 4344829 (hereinafter, Patent Literature 1) and in "Passive component based multifunctional Jones matrix swept source optical coherence tomography for Doppler and polarization imaging" OPTICS LETTER, VOL. 37, No. 11J, Jun. 1, 2012, p 1958 (hereinafter, Non-Patent Literature 1).

Patent Literature 1 discloses a technique of polarization sensitive OCT (PS-OCT). The optical tomographic device in Patent Literature 1 scans measurement light in a transverse direction, and at the same time, continuously modulates a polarization beam from a light source by using an EO modulator (a polarization modulator, an electro-optic modulator). The continuously modulated polarization beam is split into measurement light and reflected light, and OCT measurement is performed using spectral interference therebetween. Of spectral interference components, a vertical polarization component and a horizontal polarization component are simultaneously measured by two light detectors, whereby a Jones matrix representing a polarization property of a subject is acquired.

However, since the EO modulator is expensive, Non-Patent Literature 1 discloses a technique of polarization sensitive OCT that does not utilize an EO modulator. In Non-Patent Literature 1, a measurement optical system including a polarizer, two polarization beam splitters, and two dove prisms is disclosed. In the measurement optical system, light from a light source is split into horizontal polarization light and vertical polarization light, and an optical path length difference is generated between the horizontal polarization light and the vertical polarization light. The generated horizontal polarization light and the vertical polarization light are superimposed, and the resultant light is radiated to a subject. The reflected light from the subject is combined with reference light generated by a reference optical system, whereby interfering light is generated. Since the light radiated to the subject is composed of the horizontal polarization light and the vertical polarization light that are superimposed, the generated interfering light contains a first interfering light component based on a horizontal polarization component and a second interfering light component based on a vertical polarization component. The first interfering light component and the second interfering light component can be simultaneously measured by two light detectors. Thus, by adding a simple optical system instead of an EO modulator, a Jones matrix representing a polarization property of the subject is acquired.

BRIEF SUMMARY OF INVENTION

In the technique of Non-Patent Literature 1, an interfering light signal including the first interfering light component and the second interfering light component, which is delayed relative to the first interfering light component by the optical path length difference, is subjected to signal processing by an A/D converter. There is a limit on a sampling frequency of the A/D converter. In the case of the A/D converter sampling two interfering light components with different optical path lengths, namely, in different frequency regions, it is necessary to divide a sampling frequency region into two regions, to sample two interfering light components. As a result, a sampling frequency per one interfering light component is limited to a frequency region corresponding to a half range of a frequency region in which sampling can be performed. Therefore, although images of two polarization states can be acquired simultaneously, a problem arises that a measurement range (depthwise measurement range) of the optical tomographic device needs to be halved.

The present application discloses an optical tomographic device capable of simultaneously acquiring a plurality of tomographic images at a same position in a subject without narrowing a depthwise measurement range.

The optical tomographic device described in the description comprises a light source, a measurement light generator that generates measurement light by using light from the light source and that generates reflected light by irradiating the measurement light onto the subject, a reference light generator that generates reference light by using the light from the light source, an interfering light generator that generates interfering light by combining the reflected light generated in the measurement light generator and the reference light generated in the reference light generator, and an interfering light detector that detects the interfering light generated in the interfering light generator and converts the interfering light into interfering signals. The measurement light generator generates at least two measurement lights with different optical path lengths, superimposes the at least two measurement lights, irradiates the superimposed at least two measurement lights onto the subject, splits the reflected light reflected from the subject into at least two reflected lights, and guides the split at least two reflected lights to the interfering light generator, the reference light generator generates at least two reference lights with different optical path lengths, the interfering light generator includes at least two interfering light generators, each interfering light generator is configured to combine one of the at least two reflecting lights with different optical path length guided from the measurement light generator and the corresponding one of the at least two reference lights with different optical path lengths generated in the reference light generator, the interfering light detector includes at least two interfering light detectors, each interfering light detector is configured to detect the interfering light generated in the corresponding one of the at least two interfering light generators and convert the detected interfering light into the corresponding one of the at least two interfering signals.

In the above optical tomographic device, measurement light obtained by superimposing at least two measurement lights with different optical path lengths is radiated to a subject, the reflected light from the subject is split into at least two reflected lights, and the at least two reflected lights and at least two reference lights with different optical path lengths are combined, whereby at least two interfering light are generated. The at least two interfering lights are independently detected by at least two interfering light detectors, whereby at least two interfering signals are generated. Thus, it is not necessary to divide the sampling frequency of the interfering light detector. Therefore, it is possible to simultaneously acquire a plurality of tomographic images of the subject without narrowing the depthwise measurement range.

Figure 1:
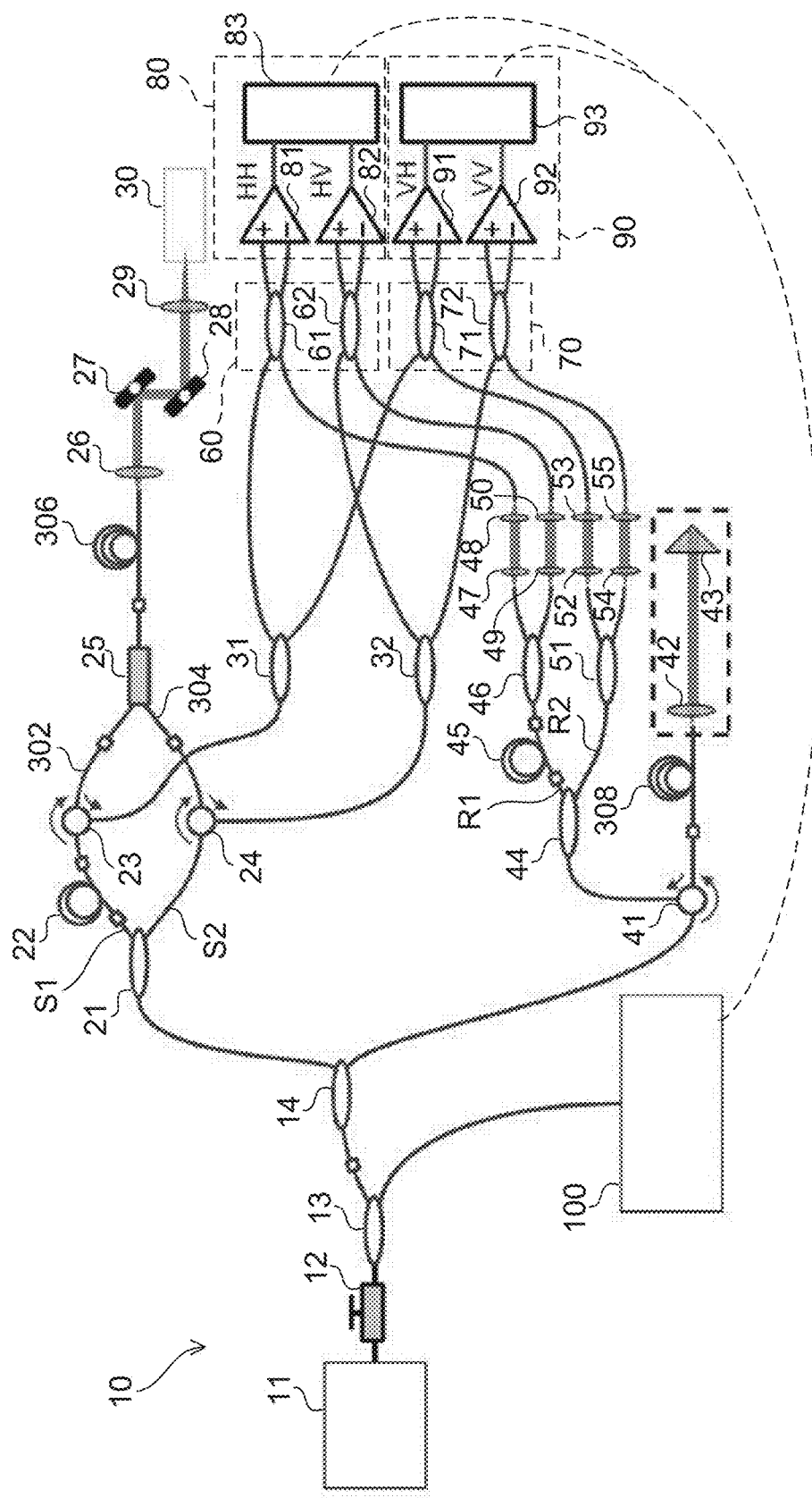
FIG. 1 is a schematic configuration diagram of an optical system of an optical tomographic device according to the present embodiment.

DETAILED DESCRIPTION OF INVENTION (First feature) In the optical tomographic device described in the description, a measurement light generator may comprise a first splitter that splits the measurement light from the light source into at least two optical paths and a first optical path length difference generator provided on the at least one of the at least two optical paths split by the first splitter. The first optical path length difference generator may be configured to generate different optical path lengths between the at least two optical paths. Such a configuration can allow for generating at least two measurement lights with different optical path lengths in a simplified manner by only providing the optical path length difference generator on at least one of at least two optical paths.

(Second feature) In the optical tomographic device described in the description, the reference light generator may comprise a second splitter that splits the reference light from the light source into at least two optical paths and a second optical path length difference generator provided on the at least one of the at least two optical paths split by the second splitter. The second optical path length difference generator may be configured to generate different optical path lengths between the at least two optical paths. Such a configuration can allow for generating at least two reference lights with different optical path lengths in a simplified manner by only providing the optical path length difference generator on at least one of at least two optical paths.

(Third feature) The optical tomographic device described in the description may comprise an image processor configured to generate one optical tomographic image from at least two optical tomographic images obtained from the at least two interfering signals obtained by the at least two interfering light detectors. Such a configuration can allow for obtaining an optical tomographic image with high quality by performing image processing such as averaging processing on the at least two optical tomographic images acquired for a same position.

(Fourth feature) In the optical tomographic device described in the description, at least one difference of optical path lengths between the at least two optical paths split in the measurement light generator and at least one difference of optical path lengths between the at least two optical paths split in the reference light generator may be the same difference. Such a configuration can allow the depthwise positions of the at least two interfering lights in the subject to coincide with each other. Thus, it becomes unnecessary to perform position adjustment between the acquired at least two tomographic images.

(Fifth feature) In the optical tomographic device described in the description, at least one difference of optical path lengths between the at least two optical paths split in the measurement light generator may be longer than a depthwise range of the subject to be measured, and at least one difference of optical path lengths between the at least two optical paths split in the reference light generator may be longer than the depthwise range of the subject to be measured. Such a configuration can allow for preventing the interfering light with different optical path lengths from overlapping each other.

(Sixth feature) In the optical tomographic device described in the description, polarization components of light in at least two different optical paths split in the measurement light generator may be different from each other. Such a configuration makes it possible to acquire a tomographic image by polarization sensitive OCT capable of recognizing a birefringence property of a subject.

(Seventh feature) In the optical tomographic device described in the description, the polarization components of the light in at least two different light paths split in the measurement light generator may include at least horizontal polarization and vertical polarization. Such a configuration can allow for acquiring a Jones matrix representing a polarization property of a subject.

(Eighth feature) In the optical tomographic device described in the description, the measurement light generator may comprise the first splitter splits the measurement light from the light source into the at least two light with polarization directions that are different from each other, and a third splitter splits the reflected light from the subject into the at least two light with polarization directions that are different from each other. At least one of the first splitter and the third splitter may be a polarization beam combiner/splitter. Such a configuration can allow for simplifying the configuration of an optical system, thereby facilitating adjustment in the optical system.

(Ninth feature) In the optical tomographic device described in the description, at least one optical path configuring an optical system of the optical tomographic device may comprise a polarization maintaining fiber. Such a configuration allows for simple configuration of an optical system for, particularly, polarization sensitive OCT.

(Embodiments)

Hereinafter, an optical tomographic device according to the present embodiment will be described. The optical tomographic device of the present embodiment is a polarization sensitive OCT (so-called PS-OCT) device capable of acquiring a polarization property of a subject, by a Fourier domain method of a wavelength sweeping type using a light source of a wavelength sweeping type (so-called SS-OCT method). The technique disclosed in the present application is not limited to polarization sensitive OCT, but is also applicable to normal OCT such as fundus OCT or anterior segment OCT. The OCT method is not limited to SS-OCT, but is also applicable to another method using a Fourier domain method, such as SD-OCT (spectrum domain OCT), or a method other than a Fourier domain method (for example, a time domain method).

As shown in FIG. 1, the optical tomographic device of the present embodiment includes: a light source 11; a measurement light generator (21 to 29, 31, 32) which generates a measurement light based on light from the light source 11; a reference light generator (41 to 46, 51) which generates reference light based on light from the light source 11; an interfering light generator 60, 70 which combines the reflected light from a subject 30 generated in the measurement light generator and the reference light generated in the reference light generator, to generate interfering light; and an interfering light detector 80, 90 which detects the interfering light generated in the corresponding interfering light generator.

(Light Source)

The light source 11 is a light source of a wavelength sweeping type, and the wavelength (wavenumber) of emitted light varies with a predetermined cycle. Since the wavelength of light radiated to the subject 30 varies (sweeps), a signal obtained from interfering light between the reflected light from the subject 30 and the reference light is subjected to Fourier analysis, and thereby an intensity distribution of light reflected from each depthwise portion of the subject 30 can be obtained.

A polarization control device 12 and a fiber coupler 13 are connected to the light source 11, and a PM (Polarization Maintaining) coupler 14 and a sampling trigger/clock generator 100 are connected to the fiber coupler 13. Therefore, light outputted from the light source 11 is inputted via the polarization control device 12 and the fiber coupler 13 to the PM coupler 14 and the sampling trigger/clock generator 100. The sampling trigger/clock generator 100 generates a sampling trigger and a sampling clock for each of signal processors 83 and 93 described later, using the light from the light source 11.

(Measurement Light Generator)

The measurement light generator (21 to 29, 31, 32) includes: a PM coupler 21 connected to the PM coupler 14; two measurement light paths S1 and S2 split from the PM coupler 21; a polarization beam combiner/splitter 25 connecting the two measurement light paths S1 and S2; and a collimator lens 26, an optical path extension portion 306, galvanometer mirrors 27 and 28, and a lens 29 which are connected to the polarization beam combiner/splitter 25. An optical path length difference generator 22 and a circulator 23 are provided on the measurement light path S1. Only a circulator 24 is provided on the measurement light path S2. Therefore, an optical path length difference Δ1 between the measurement light path S1 and the measurement light path S2 is generated by the optical path length difference generator 22. The optical path length difference Δ1 may be set to be longer than a depthwise measurement range of a subject. Thus, interfering light with different optical path lengths can be prevented from overlapping each other. For the optical path length difference generator 22, for example, an optical fiber may be used, or an optical system such as a mirror or a prism may be used. In the present embodiment, a PM fiber that is one meter long is used for the optical path length difference generator 22. The measurement light generator further includes PM couplers 31 and 32. The PM coupler 31 is connected to the circulator 23. The PM coupler 32 is connected to the circulator 24.

One light (that is, measurement light) split by the PM coupler 14 is inputted to the measurement light generator (21 to 29, 31, 32). The PM coupler 21 divides the measurement light inputted from the PM coupler 14, into first measurement light and second measurement light. The first measurement light divided by the PM coupler 21 is guided to the measurement light path S1, and the second measurement light divided by the PM coupler 21 is guided to the measurement light path S2. The first measurement light guided to the measurement light path S1 is inputted through the optical path length difference generator 22 and the circulator 23 to the polarization beam combiner/splitter 25. The second measurement light guided to the measurement light path S2 is inputted through the circulator 24 to the polarization beam combiner/splitter 25. A PM fiber 304 is connected to the polarization beam combiner/splitter 25 such that the PM fiber 304 is turned by 90 degrees in the circumferential direction relative to a PM fiber 302. Thus, the second measurement light inputted to the polarization beam combiner/splitter 25 has a polarization component orthogonal to that of the first measurement light. Since the optical path length difference generator 22 is provided on the measurement light path S1, the first measurement light is delayed relative to the second measurement light by a distance corresponding to the optical path length difference generator 22 (that is, the optical path length difference Δ1 is generated). The polarization beam combiner/splitter 25 superimposes the first measurement light and the second measurement light inputted thereto. The light (the light composed of the first measurement light and the second measurement light that have been superimposed) outputted from the polarization beam combiner/splitter 25 is radiated to the subject 30 via the collimator lens 26, the galvanometer mirrors 27 and 28, and the lens 29. The optical path extension portion 306 may be provided between the collimator lens 26 and the galvanometer mirror 27. For the optical path extension portion 306, for example, a PM fiber that is about 60 meters long may be used as shown in FIG. 1. Thus, occurrence of crosstalk between two modes of the PM fiber can be suppressed. The light to be radiated to the subject 30 is scanned along an x-y direction by the galvanometer mirrors 27 and 28.

The light radiated to the subject 30 is reflected by the subject 30. Here, the light to be reflected by the subject 30 is scattered on a surface of the subject 30 or inside the subject 30. The reflected light from the subject 30, in a reverse direction to an entering direction of the light path, passes through the lens 29, the galvanometer mirrors 28 and 27, and the collimator lens 26, and then is inputted to the polarization beam combiner/splitter 25. The polarization beam combiner/splitter 25 divides the inputted reflected light into horizontal polarization reflected light (horizontal polarization component) and vertical polarization reflected light (vertical polarization component) which are polarization components orthogonal to each other, so that the horizontal polarization reflected light is guided to the measurement light path S1 and the vertical polarization reflected light is guided to the measurement light path S2.

The optical path of the horizontal polarization reflected light is changed by the circulator 23, whereby the horizontal polarization reflected light is inputted to the PM coupler 31. The PM coupler 31 splits the inputted horizontal polarization reflected light so as to be inputted to each of PM couplers 61 and 71. Therefore, the horizontal polarization reflected light inputted to each of the PM couplers 61 and 71 contains a reflected light component based on the first measurement light and a reflected light component based on the second measurement light.

The optical path of the vertical polarization reflected light is changed by the circulator 24, so that the vertical polarization reflected light is inputted to the PM coupler 32. The PM coupler 32 splits the inputted vertical polarization reflected light so as to be inputted to each of PM couplers 62 and 72. Therefore, the vertical polarization reflected light inputted to each of the PM couplers 62 and 72 contains a reflected light component based on the first measurement light and a reflected light component based on the second measurement light.

(Reference Light Generator)

The reference light generator (41 to 46, 51) includes: a circulator 41 connected to the PM coupler 14; a reference delay line (42, 43) connected to the circulator 41; a PM coupler 44 connected to the circulator 41; two reference light paths R1 and R2 split from the PM coupler 44; a PM coupler 46 connected to the reference light path R1; and a PM coupler 51 connected to the reference light path R2. An optical path length difference generator 45 is provided on the reference light path R1. No optical path length difference generator is provided on the reference light path R2. Therefore, an optical path length difference $\Delta1'$ between the reference light path R1 and the reference light path R2 is generated by the optical path length difference generator 45. For example, an optical fiber is used for the optical path length difference generator 45. The optical path length difference $\Delta1'$ of the optical path length difference generator 45 may be the same as the optical path length difference $\Delta1$ of the optical path length difference generator 22. If the optical path length differences $\Delta1$ and $\Delta1'$ are the same, depthwise positions of a plurality of interfering light described later in the subject coincide with each other. That is, it becomes unnecessary to perform position adjustment among a plurality of acquired tomographic images.

The other light (that is, reference light) split by the PM coupler 14 is inputted to the reference light generator (41 to 46, 51). The reference light inputted from the PM coupler 14 is inputted through the circulator 41 to the reference delay line (42, 43). An optical path extension portion 308 may be provided between the light circulator 41 and the reference delay line (42, 43). A PM fiber that is about 60 meters long may be used for the optical path extension portion 308 as shown in FIG. 1. The reference delay line (42, 43) is composed of a collimator lens 42 and a reference mirror 43. The reference light inputted to the reference delay line (42, 43) is radiated via the collimator lens 42 to the reference mirror 43. The reference light reflected by the reference mirror 43 is inputted via the collimator lens 42 to the circulator 41. Here, the reference mirror 43 is movable along a direction to approach or be separated from the collimator lens 42. In the present embodiment, before measurement is started, the position of the reference mirror 43 is adjusted so that an optical path length (measurement light path length) from the PM coupler 14 through the measurement light path S2 to the subject 30 coincides with an optical path length (reference light path length) from the PM coupler 14 to the reference mirror 43.

The optical path of the reference light reflected by the reference mirror 43 is changed by the circulator 41, so that the reference light is inputted to the PM coupler 44. The PM coupler 44 splits the inputted reference light into first reference light and second reference light. The first reference light is guided to the reference light path R1, and the second reference light is guided to the reference light path R2. The first reference light is inputted through the optical path length difference generator 45 to the PM coupler 46. The reference light inputted to the PM coupler 46 is split into first split reference light and second split reference light. The first split reference light is inputted through a collimator lens 47 and a lens 48 to the PM coupler 61. The second split reference light is inputted through a collimator lens 49 and a lens 50 to the PM coupler 62. The second reference light is inputted to the PM coupler 51, and is divided into third split reference light and fourth split reference light. The third split reference light is inputted through a collimator lens 52 and a lens 53 to the PM coupler 71. The fourth split reference light is inputted through a collimator lens 54 and a lens 55 to the PM coupler 72.

(Interfering Light Generator)

The interfering light generator 60, 70 includes a first interfering light generator 60 and a second interfering light generator 70. The first interfering light generator 60 includes the PM couplers 61 and 62. As described above, the PM coupler 61 receives the horizontal polarization reflected light from the measurement light generator, and receives the first split reference light (light having the optical path length difference $\Delta1$) from the reference light generator. Here, the horizontal polarization reflected light contains the reflected light component (light having the optical path length difference $\Delta1$) based on the first measurement light, and the reflected light component (light not having the optical path length difference $\Delta1$) based on the second measurement light. Therefore, in the PM coupler 61, of the horizontal polarization reflected light, the reflected light component (light having the optical path length difference $\Delta1$) based on the first measurement light, and the first split reference light are combined, whereby first interfering light (horizontal polarization component) is generated.

The PM coupler 62 receives the vertical polarization reflected light from the measurement light generator, and receives the second split reference light (light having the optical path length difference $\Delta1$) from the reference light generator. Here, the vertical polarization reflected light contains the reflected light component (light having the optical path length difference $\Delta1$) based on the first measurement light, and the reflected light component (light not having the optical path length difference $\Delta1$) based on the second measurement light. Therefore, in the PM coupler 62, of the vertical polarization reflected light, the reflected light component (light having the optical path length difference $\Delta1$) based on the first measurement light, and the second split reference light are combined, whereby second interfering light (vertical polarization component) is generated.

The second interfering light generator 70 includes the PM couplers 71 and 72. As described above, the PM coupler 71 receives the horizontal polarization reflected light from the measurement light generator, and receives the third split reference light (light not having the optical path length difference $\Delta1$) from the reference light generator. Therefore, in the PM coupler 71, of the horizontal polarization reflected light, the reflected light component (light not having the optical path length difference Δ1) based on the second measurement light, and the third split reference light are combined, whereby third interfering light (horizontal polarization component) is generated.

The PM coupler 72 receives the vertical polarization reflected light from the measurement light generator, and receives the fourth split reference light (light not having the optical path length difference Δ1) from the reference light generator. Therefore, in the PM coupler 72, of the vertical polarization reflected light, the reflected light component (light not having the optical path length difference Δ1) based on the second measurement light, and the fourth split reference light are combined, whereby fourth interfering light (vertical polarization component) is generated. The first interfering light and the second interfering light correspond to the measurement light that has passed through the measurement light path S1, and the third interfering light and the fourth interfering light correspond to the measurement light that has passed through the measurement light path S2.

(Interfering Light Detector)

The interfering light detector 80, 90 includes a first interfering light detector 80 which detects the interfering light (the first interfering light and the second interfering light) generated in the first interfering light generator 60, and a second interfering light detector 90 which detects the interfering light (the third interfering light and the fourth interfering light) generated in the second interfering light generator 70.

The first interfering light detector 80 includes balanced light detectors 81 and 82, and a signal processor 83 connected to the balanced light detectors 81 and 82. The PM coupler 61 is connected to the balanced light detector 81, and the signal processor 83 is connected to an output terminal of the balanced light detector 81. The PM coupler 61 splits the first interfering light into two interfering light having phases different from each other by 180 degrees, and inputs the two interfering light to the balanced light detector 81. The balanced light detector 81 performs differential amplification processing and noise reduction processing for the two interfering light having phases different from each other by 180 degrees inputted from the PM coupler 61, so as to be converted to an electric signal (first interfering signal), and outputs the first interfering signal to the signal processor 83. That is, the first interfering signal is an interfering signal HH between the horizontal polarization reflected light from the subject based on the horizontal polarization measurement light, and the reference light. Similarly, the PM coupler 62 is connected to the balanced light detector 82, and the signal processor 83 is connected to an output terminal of the balanced light detector 82. The PM coupler 62 splits the second interfering light into two interfering light having phases different from each other by 180 degrees, and inputs the two interfering light to the balanced light detector 82. The balanced light detector 82 performs differential amplification processing and noise reduction processing for the two interfering light having phases different from each other by 180 degrees, so as to be converted to an electric signal (second interfering signal), and outputs the second interfering signal to the signal processor 83. That is, the second interfering signal is an interfering signal HV between the vertical polarization reflected light from the subject based on the horizontal polarization measurement light, and the reference light. The signal processor 83 samples the first interfering signal (a signal based on the first interfering light) and the second interfering signal (a signal based on the second interfering light), based on a sampling trigger and a sampling clock inputted from the sampling trigger/clock generator 100. The first interfering signal and the second interfering signal sampled by the signal processor 83 are inputted to a calculation unit 200 described later. A known data acquiring device (so-called DAQ) may be used for the signal processor 83.

The second interfering light detector 90, similarly to the first interfering light detector 80, includes balanced light detectors 91 and 92, and a signal processor 93 connected to the balanced light detectors 91 and 92. The PM coupler 71 is connected to the balanced light detector 91, and the signal processor 93 is connected to an output terminal of the balanced light detector 91. The PM coupler 71 splits the third interfering light into two interfering light having phases different from each other by 180 degrees, and inputs the two interfering light to the balanced light detector 91. The balanced light detector 91 performs differential amplification processing and noise reduction processing for the two interfering light having phases different from each other by 180 degrees, so as to be converted to an electric signal (third interfering signal), and outputs the third interfering signal to the signal processor 93. That is, the third interfering signal is an interfering signal VH between the horizontal polarization reflected light from the subject based on the vertical polarization measurement light, and the reference light. Similarly, the PM coupler 72 is connected to the balanced light detector 92, and the signal processor 93 is connected to an output terminal of the balanced light detector 92. The PM coupler 72 splits the fourth interfering light into two interfering light having phases different from each other by 180 degrees, and inputs the two interfering light to the balanced light detector 92. The balanced light detector 92 performs differential amplification processing and noise reduction processing for the two interfering light having phases different from each other by 180 degrees, so as to be converted to an electric signal (fourth interfering signal), and outputs the fourth interfering signal to the signal processor 93. That is, the fourth interfering signal is an interfering signal VV between the vertical polarization reflected light from the subject based on the vertical polarization measurement light, and the reference light. The signal processor 93 samples the third interfering signal (a signal based on the third interfering light) and the fourth interfering signal (a signal based on the fourth interfering light), based on a sampling trigger and a sampling clock inputted from the sampling trigger/clock generator 100. The third interfering signal and the fourth interfering signal sampled by the signal processor 93 are inputted to the calculation unit 200 described later. A known data acquiring device (so-called DAQ) may be used also for the signal processor 93. By the above configuration, interfering signals indicating four polarization properties of the subject 30 can be acquired.

Figure 2:
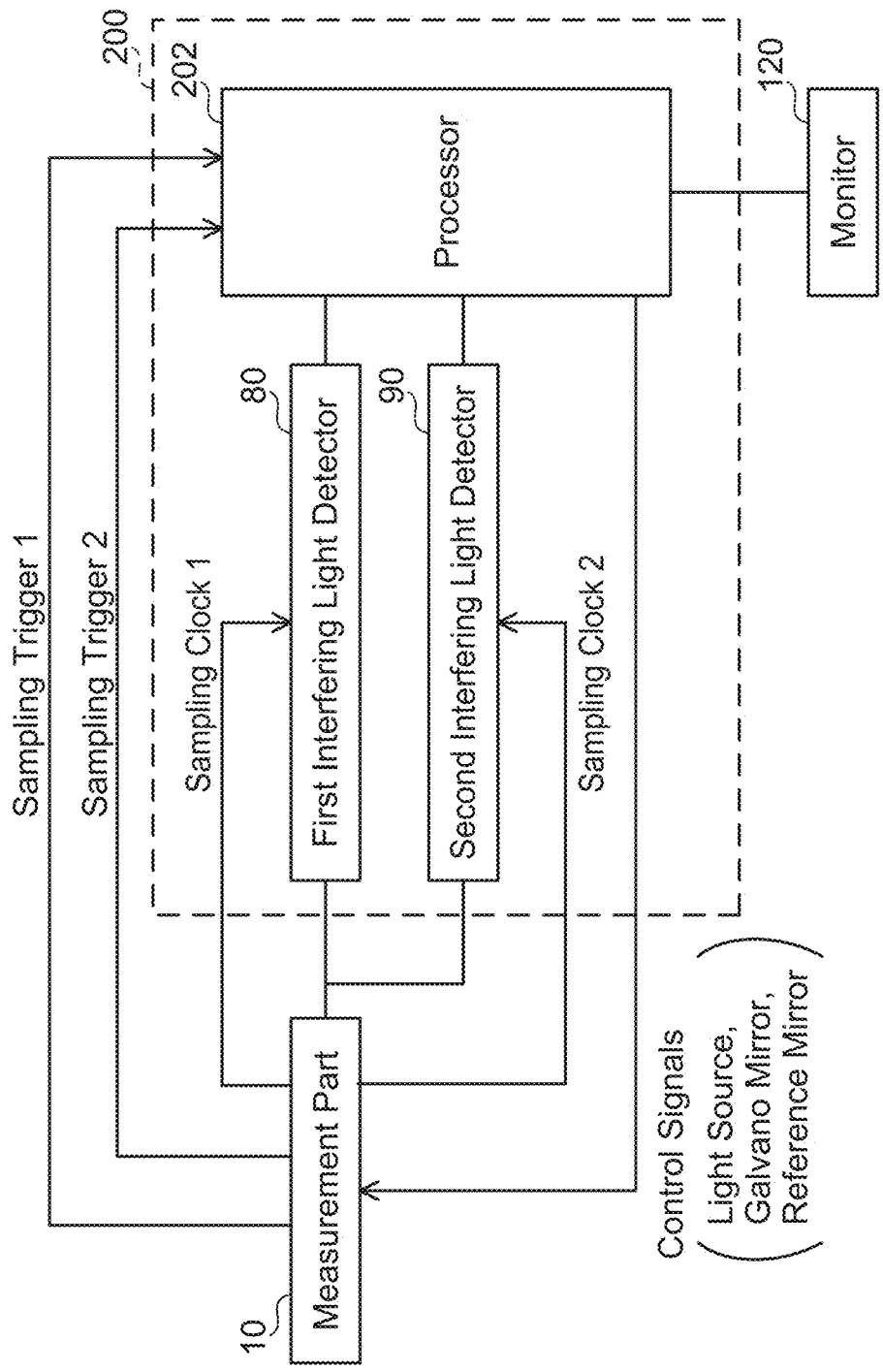
FIG. 2 is a block diagram of a control system of the optical tomographic device according to the present embodiment.

Next, the configuration of a control system of the optical tomographic device according to the present embodiment will be described. As shown in FIG. 2, the optical tomographic device is controlled by the calculation unit 200. The calculation unit 200 includes a processor 202, the first interfering light detector 80, and the second interfering light detector 90. The first interfering light detector 80, the second interfering light detector 90, and the processor 202 are connected to a measurement part 10. The processor 202 outputs a control signal to the measurement part 10, to drive the galvanometer mirrors 27 and 28, thereby moving the incidence position of measurement light on the subject 30. The first interfering light detector 80 acquires first sampling data with respect to the interfering signals (interfering signal HH and interfering signal HV) inputted from the measurement part 10, based on a sampling clock 1 inputted from the measurement part 10, using a sampling trigger 1 as a trigger, and outputs the first sampling data to the processor 202. The processor 202 performs calculation processing such as Fourier transform processing on the first sampling data, to generate an HH tomographic image and an HV tomographic image. The second interfering light detector 90 acquires second sampling data with respect to the interfering signals (interfering signal VH and interfering signal VV) inputted from the measurement part 10, based on a sampling clock 2 inputted from the measurement part 10, using a sampling trigger 2 as a trigger, and outputs the second sampling data to the processor 202. The processor 202 performs calculation processing such as Fourier transform processing on the second sampling data, to generate a VH tomographic image and a VV tomographic image. Here, the HH tomographic image, the VH tomographic image, the HV tomographic image, and the VV tomographic image are tomographic images at a same position. Therefore, the processor 202 can generate tomographic images of four polarization properties (HH, HV, VH, VV) representing a Jones matrix of the subject 30.

Figure 3:
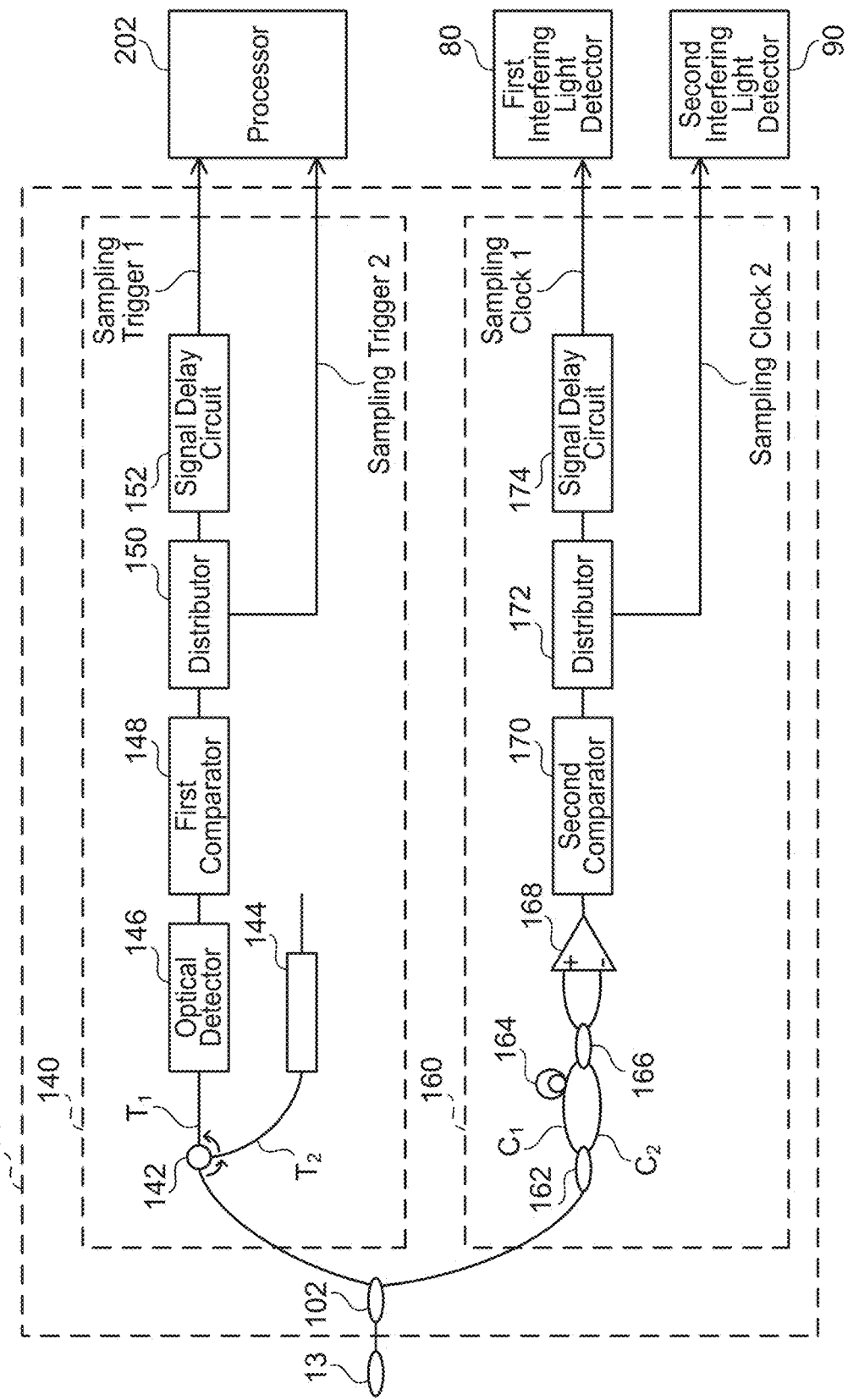
FIG. 3 is a block diagram showing a detailed configuration of a sampling trigger/clock generator according to the present embodiment.

As shown in FIG. 3, the sampling trigger/clock generator 100 includes a fiber coupler 102, a sampling trigger generator (140 to 152), and a sampling clock generator (160 to 172). Light from the light source is inputted via the fiber coupler 13 and the fiber coupler 102 to each of the sampling trigger generator 140 and the sampling clock generator 160.

(Sampling Trigger Generator)

The sampling trigger generator 140 may generate a sampling trigger by using, for example, an FBG (Fiber Bragg Grating) 144. As shown in FIG. 3, the FBG 144 reflects only a component having a specific wavelength, of light inputted from the light source 11, thereby generating a sampling trigger. The generated sampling trigger is inputted to a distributor 150. The distributor 150 distributes the sampling trigger into the sampling trigger 1 and the sampling trigger 2. The sampling trigger 1 is inputted via a signal delay circuit 152 to the processor 202. The sampling trigger 2 is directly inputted to the processor 202. The sampling trigger 1 is a trigger signal for the interfering signals (first interfering signal and second interfering signal) inputted from the first interfering light detector 80 to the processor 202. The sampling trigger 2 is a trigger signal for the interfering signals (third interfering signal and fourth interfering signal) inputted from the second interfering light detector 90 to the processor 202. The signal delay circuit 152 is designed so that the sampling trigger 1 is delayed relative to the sampling trigger 2 by a time corresponding to the optical path length difference Δ1 of the optical path length difference generator 22. Thus, a frequency at which sampling of the interfering signals inputted from the first interfering light detector 80 is started and a frequency at which sampling of the interfering signals inputted from the second interfering light detector 90 is started can be made same. Here, only the sampling trigger 1 may be generated. Since the optical path length difference Δ1 is already known, in the case of sampling the interfering signals inputted from the second interfering light detector 90, the sampling may be started with a delay from the sampling trigger 1 by a time corresponding to the optical path length difference Δ1.

(Sampling Clock Generator)

The sampling clock generator may be composed of a Mach-Zehnder interferometer, for example. As shown in FIG. 3, the sampling clock generator generates a sampling clock with an equal frequency, using a Mach-Zehnder interferometer. The sampling clock generated by the Mach-Zehnder interferometer is inputted to a distributor 172. The distributor 172 distributes the sampling clock into the sampling clock 1 and the sampling clock 2. The sampling clock 1 is inputted through a signal delay circuit 174 to the first interfering light detector 80. The sampling clock 2 is directly inputted to the second interfering light detector 90. The signal delay circuit 174 is designed so as to cause a delay by a time corresponding to the optical path length difference Δ1 of the optical path length difference generator 22. Thus, the interfering light with the delay corresponding to the optical path length difference generator 22 can also be sampled at a same timing. Thus, the positions of a plurality of acquired tomographic images can be prevented from being misaligned from each other. In the present embodiment, a Mach-Zehnder interferometer is used for generating sampling clocks. Alternatively, for generating sampling clocks, a Michelson interferometer may be used or an electric circuit may be used. Alternatively, sampling clocks may be generated by using a light source having a sampling clock generator.

As shown from the above description, in the optical tomographic device according to the present embodiment, it is not necessary to divide the sampling frequency into two regions in order to perform signal processing of the interfering signals by the signal processors 83 and 93. Therefore, it is possible to sample the interfering signals up to the frequency at which the signal processors 83 and 93 can perform sampling. Thus, the depthwise measurement range can be doubled as compared to the optical tomographic device disclosed in Non-Patent Literature 1, for example.

Specific examples of the present invention has been described in detail, however, these are mere exemplary indications and thus do not limit the scope of the claims. The art described in the claims include modifications and variations of the specific examples presented above.

(Modification 1)

Figure 4:
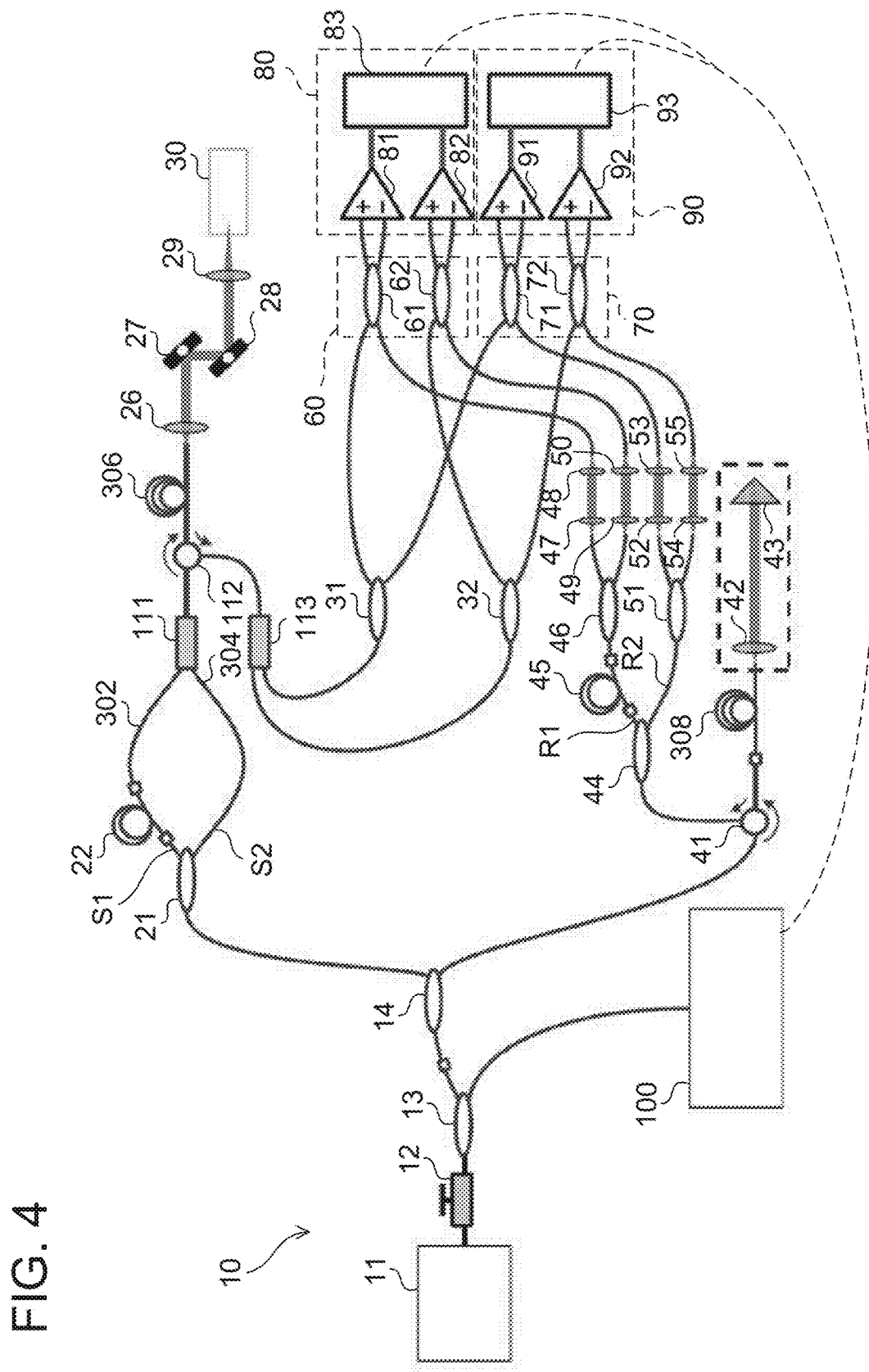
FIG. 4 is a schematic configuration diagram of an optical system of an optical tomographic device according to modification 1.

For example, the configuration of the optical system of the optical tomographic device is not limited to the configuration shown in FIG. 1, but various configurations may be employed. For example, a configuration as shown in FIG. 4 may be employed. In the optical tomographic device shown in FIG. 4, a configuration from the PM coupler 14 to the PM couplers 31 and 32 is different from that in the above embodiment.

That is, the measurement light split at the PM coupler 14 is inputted to the polarization beam splitter 21 and thereby split into the first measurement light (horizontal polarization component) and the second measurement light (vertical polarization component). The first measurement light is guided to the measurement light path S1, and the second measurement light is guided to the measurement light path S2. The first measurement light is inputted through the optical path length difference generator 22 to a polarization beam combiner 111. The second measurement light is inputted through the measurement light path S2 to the polarization beam combiner 111. The first measurement light and the second measurement light are superimposed by the polarization beam combiner 111, and the resultant light passes through a circulator 112 and then is radiated to the subject 30.

The reflected light from the subject 30, in a reverse direction to an entering direction of the light path, passes through the lens 29, the galvanometer mirrors 28 and 27, and the collimator lens 26, and then the optical path of the reflected light is changed by the circulator 112, so that the reflected light is inputted to a polarization beam splitter 113. In the polarization beam splitter 113, the reflected light is split into the first reflected light (horizontal polarization component) and the second reflected light (vertical polarization component). Such a configuration can allow for also providing the same operation and effect as that in the above embodiment.

(Modification 2)

Figure 5:
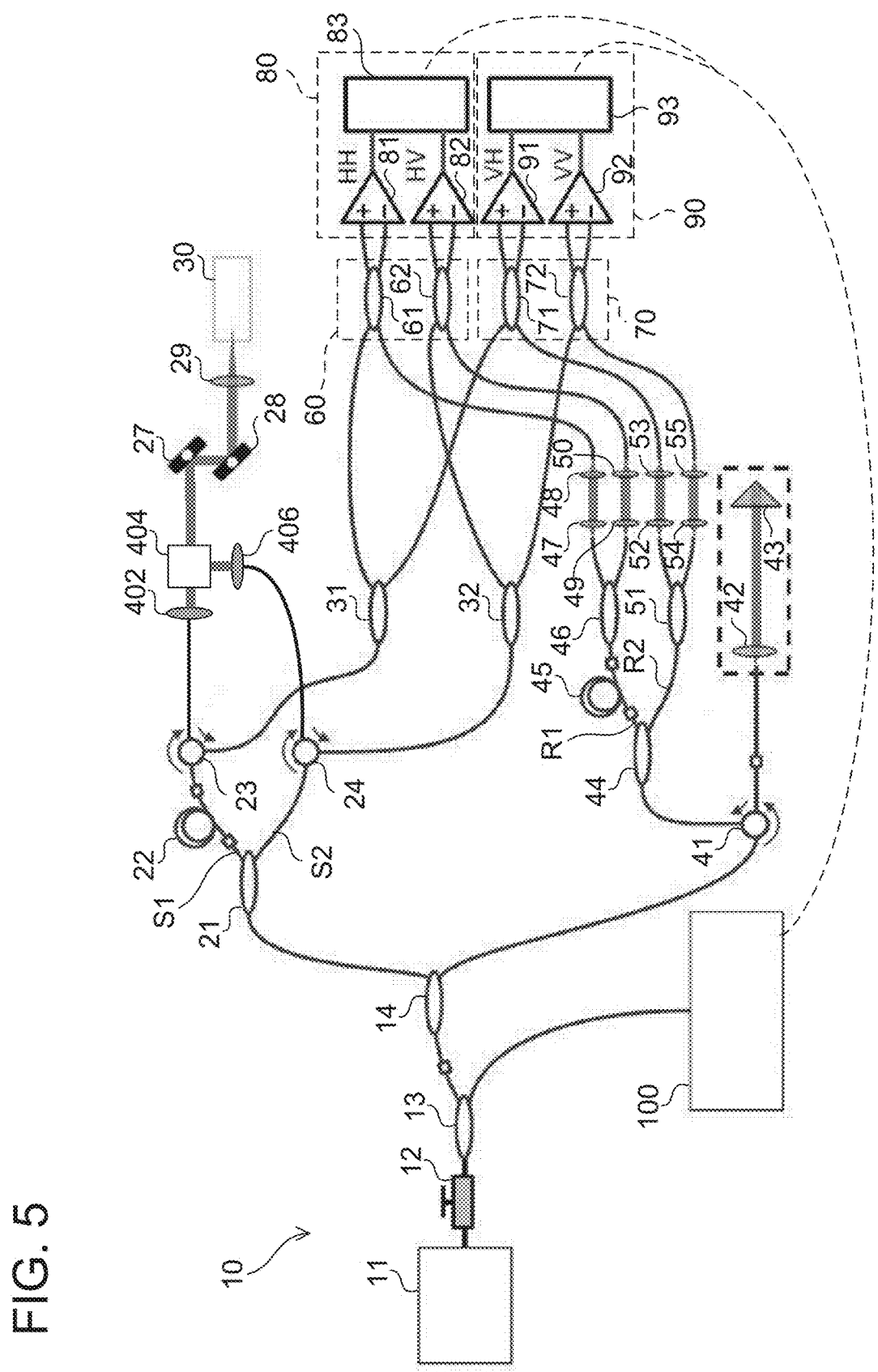
FIG. 5 is a schematic configuration diagram of an optical system of an optical tomographic device according to modification 2.

The optical system of the optical tomographic device may be configured as shown in FIG. 5. The optical tomographic device shown in FIG. 5 is different from the above embodiment in the configuration from the polarization beam combiner/splitter 25 to the subject 30 in FIG. 1. That is, in this modification, a polarization beam splitter 404 is used instead of the polarization beam combiner/splitter 25.

The measurement light split at the PM coupler 14 is split into the first measurement light and the second measurement light by the PM coupler 21. The first measurement light is guided to the measurement light path S1, and the second measurement light is guided to the measurement light path S2. The first measurement light is inputted through the optical path length difference generator 22 and a collimator lens 402 to the polarization beam splitter 404. The second measurement light is inputted through the measurement light path S2 and a collimator lens 406 to the polarization beam splitter 404. A PM fiber is connected to the collimator lens 406 such that the PM fiber is turned by 90 degrees. The first measurement light and the second measurement light are superimposed by the polarization beam splitter 404, and the resultant light is radiated to the subject 30 via the galvanometer mirrors 27 and 28 and the collimator lens 29. The light radiated to the subject 30 is reflected by the subject 30. Here, the light from the subject 30, in a reverse direction to an entering direction of the light path, passes through the collimator lens 29 and the galvanometer mirrors 28 and 27, and then is inputted to the polarization beam splitter 404. The polarization beam splitter 404 divides the inputted reflected light into horizontal polarization reflected light (horizontal polarization component) and vertical polarization reflected light (vertical polarization component) which are polarization components orthogonal to each other. Then, the horizontal polarization reflected light is guided to the measurement light path S1, and the vertical polarization reflected light is guided to the measurement light path S2. Thus, the same operation and effect as in FIG. 1 can be provided. In such a configuration, since the polarization beam splitter 404 is used, occurrence of crosstalk between two modes of the PM fiber is suppressed. Therefore, it is not necessary to interpose the optical path extension portions 306 and 308 shown in FIG. 1 or FIG. 4.

(Modification 3)

In the optical tomographic device of the above embodiment, a wave plate, e.g., a quarter-wave plate may be provided between the collimator lens 26 and the subject 30. Such a configuration can equalize the intensities of the first to fourth interfering signals to be inputted to the signal processors 83 and 93. Thus, the first to fourth interfering signals can be measured with an optimum SNR.

(Modification 4)

In the above embodiment, the case of using a polarization sensitive OCT (PS-OCT) has been described as an example. Alternatively, as described above, the configuration according to the present invention is not limited to the polarization sensitive OCT, and as a matter of course, is also applicable to normal OCT such as fundus OCT or anterior segment OCT. In the above embodiment, the case of generating two measurement light with different optical path lengths to take an optical tomographic image has been described. Alternatively, a number of the measurement light to be generated is not limited to two, and three or more measurement light with different optical path lengths may be generated. For example, in the case of using three measurement light with different optical path lengths, three reference light corresponding to these measurement light may be generated, and three interfering light generators and three interfering light detectors corresponding to the respective optical path lengths may be provided. Thus, a plurality of tomographic images can be acquired at the same position in a subject, and if these tomographic images are subjected to image processing such as addition processing, a tomographic image with a high contrast and an optimum SNR can be acquired.

Technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

The PM coupler 21, the PM coupler 44, and the polarization beam combiner/splitter 25 are examples of the "first splitter", the "second splitter", and the "third splitter", respectively.

What is claimed is:

1. An optical tomographic device configured to acquire a tomographic image of a subject, the optical tomographic device comprising:
   a light source;
   a measurement light generator that generates measurement light by using light from the light source, and that generates reflected light by irradiating the measurement light onto the subject;
   a reference light generator that generates reference light by using the light from the light source;
   an interfering light generator that generates interfering light by combining the reflected light generated in the measurement light generator and the reference light generated in the reference light generator; and
   an interfering light detector that detects the interfering light generated in the interfering light generator and converts the interfering light into interfering signals;
   wherein the measurement light generator generates at least two measurement light with different optical path lengths, superimposes the at least two measurement light, irradiates the superimposed at least two measurement light onto the subject, splits the reflected light reflected from the subject into at least two reflected light, and guides the split at least two reflected light to the interfering light generator,
   the reference light generator generates at least two reference light with different optical path lengths,
   the interfering light generator includes at least two interfering light generators, each interfering light generator is configured to combine one of the at least two reflecting light with different optical path lengths guided from the measurement light generator and the corresponding one of the at least two reference light with different optical path lengths generated in the reference light generator,
   the interfering light detector includes at least two interfering light detectors, each interfering light detector is configured to detect the interfering light generated in the corresponding one of the at least two interfering light generators and convert the detected interfering light into the corresponding one of the at least two interfering signals.

2. The optical tomographic device according to claim 1, wherein
the measurement light generator comprises:
a first splitter that splits the measurement light from the light source into at least two optical paths; and
a first optical path length difference generator provided on the at least one of the at least two optical paths split by the first splitter, and
the first optical path length difference generator is configured to generate different optical path length between the at least two optical paths.

3. The optical tomographic device according to claim 2, wherein
the reference light generator comprises:
a second splitter that splits the reference light from the light source into at least two optical paths; and
a second optical path length difference generator provided on the at least one of the at least two optical paths split by the second splitter, and
the second optical path length difference generator is configured to generate different optical path length between the at least two optical paths.

4. The optical tomographic device according to claim 3, further comprising:
an image processor configured to generate one optical tomographic image from at least two optical tomographic images obtained from the at least two interfering signals obtained by the at least two interfering light detectors.

5. The optical tomographic device according to claim 3, wherein
at least one difference of optical path lengths between the at least two optical paths split in the measurement light generator and at least one difference of optical path lengths between the at least two optical paths split in the reference light generator are the same difference.

6. The optical tomographic device according to claim 5, wherein
at least one difference of optical path lengths between the at least two optical paths split in the measurement light generator is longer than a depthwise range of the subject to be measured, and at least one difference of optical path lengths between the at least two optical paths split in the reference light generator is longer than the depthwise range of the subject to be measured.

7. The optical tomographic device according to claim 3, wherein
at least one difference of optical path lengths between the at least two optical paths split in the measurement light generator is longer than a depthwise range of the subject to be measured, and at least one difference of optical path lengths between the at least two optical paths split in the reference light generator is longer than the depthwise range of the subject to be measured.

8. The optical tomographic device according to claim 2, wherein
polarization components of the light in the at least two different light paths split in the measurement light generator include at least horizontal polarization and vertical polarization.

9. The optical tomographic device according to claim 1, wherein
at least one optical path comprises a polarization maintaining fiber.

10. The optical tomographic device according to claim 1, further comprising:
a processor configured to generate one optical tomographic image from at least two optical tomographic images obtained from the at least two interfering signals obtained by the at least two interfering light detectors.

* * * * *